United States Patent [19]

Babil et al.

[11] 4,246,641
[45] Jan. 20, 1981

[54] AUTOMATIC TEMPERATURE CALIBRATION OF THERMAL ANALYZERS

[75] Inventors: Simon Babil, Trumbull; Andrew R. Muir, Wilton, both of Conn.

[73] Assignee: The Perkin-Elmer Corporation, Norwalk, Conn.

[21] Appl. No.: 15,556

[22] Filed: Feb. 26, 1979

[51] Int. Cl.³ .............................................. G01K 7/10
[52] U.S. Cl. ................................... 364/571; 364/557; 364/477; 364/503; 73/15 R
[58] Field of Search ............... 364/571, 557, 496, 499, 364/503, 477; 73/15 R, 15 A

[56] References Cited

U.S. PATENT DOCUMENTS

| | | | |
|---|---|---|---|
| 4,000,643 | 1/1977 | Pearson | 364/557 X |
| 4,059,982 | 11/1977 | Bowman | 364/557 X |
| 4,099,240 | 7/1978 | Rode et al. | 364/571 |
| 4,122,719 | 10/1978 | Carlson et al. | 364/557 X |

*Primary Examiner*—Edward J. Wise
*Attorney, Agent, or Firm*—Salvatore A. Giarratana; Francis L. Masselle; Edwin T. Grimes

[57] ABSTRACT

A system for use in thermal analysis for correcting discrepancies between oven temperature and desired sample temperature including means for automatically calibrating the system at several selected points in the analytical temperature scale wherein actual sample temperature is forced to agree exactly with desired sample temperature by appropriately changing oven temperature and wherein the calibrated sample temperature and the difference between oven temperature and sample temperature at the several points are used to correct for discrepancies throughout the intervening analytical temperature scale.

15 Claims, 3 Drawing Figures

AUTOMATIC TEMPERATURE CALIBRATION OF THERMAL ANALYZERS

BACKGROUND OF THE INVENTION

Thermal analyzers are utilized to test and measure characteristics of materials at various temperatures. Materials undergo significant changes at various temperatures over a wide temperatures range. For example, characteristics such as size, color, weight, electrical and magnetic properties and the like may change significantly at one or more temperatures to which a sample is heated or cooled. It is important to know the precise temperatures at which these characteristics undergo change.

The sample materials to be tested are disposed in a furnace or oven and heated or cooled over a temperature range during analysis. However, due to such effects as poor thermal coupling, thermal gradients, oven geometry and the like, the temperature of the test sample and the oven can be different. This temperature difference is normally minimized by manually calibrating at two points within the measurement temperature range. Thus, at two points actual sample temperature is made equal to the required sample temperature by raising or lowering the oven temperature. This is a tedious and time consuming method since calibration at one point disturbs calibration at the other point and much trial and error manipulation is required before adequate calibration is achieved manually. After calibration, it is known at what temperature the oven must be maintained at the calibration points to keep the sample at the selected temperature at those points. When the selected sample temperature is not at one of the calibration points, the offsets at both calibration points are used to progressively affect the oven temperature to maintain the sample at the approximate required temperature.

The present invention contemplates a thermal analyzer system having means for automatically calibrating the system wherein the sample and programmed temperature are made equal at three points and which approximates a correction for the rest of the temperature scale.

SUMMARY OF THE INVENTION

The present invention relates to a thermal analyzing system wherein a test sample is heated or cooled to various temperatures and at various rates in an oven. The system includes automatic calibration means wherein actual sample temperature is made to agree with selected sample temperature at three points in the range of temperatures within which the sample is to be tested. Each point is calibrated separately by digital electronic means wherein desired temperature is entered and compared with actual sample temperature. The difference between desired and actual sample temperatures is used to update a register containing the originally entered temperature. This process is repeated until actual sample temperature equals the entered temperature. The adjusted oven temperature necessary to force the actual sample temperature to equal the entered temperature is obtained by adding the multiplicand of a selected temperature ramp rate and elapsed time to the initial temperature of the system until the entered temperature equals actual sample temperature. During each cycle until final equilibrium is produced, the register containing the initial temperature is updated by the temperature originally storing the entered temperature incremented by the difference between the entered temperature and actual sample temperature.

After the three points are calibrated by such means, the three entered temperatures and the differences between the oven temperatures and the entered temperatures are stored in a computer memory and used to provide a correction factor over the rest of the test temperature scale.

DRAWINGS

The foregoing features as well as other features of the invention will become more apparent with reading the following description in conjunction with the drawings wherein.

DESCRIPTION

Figure 1:
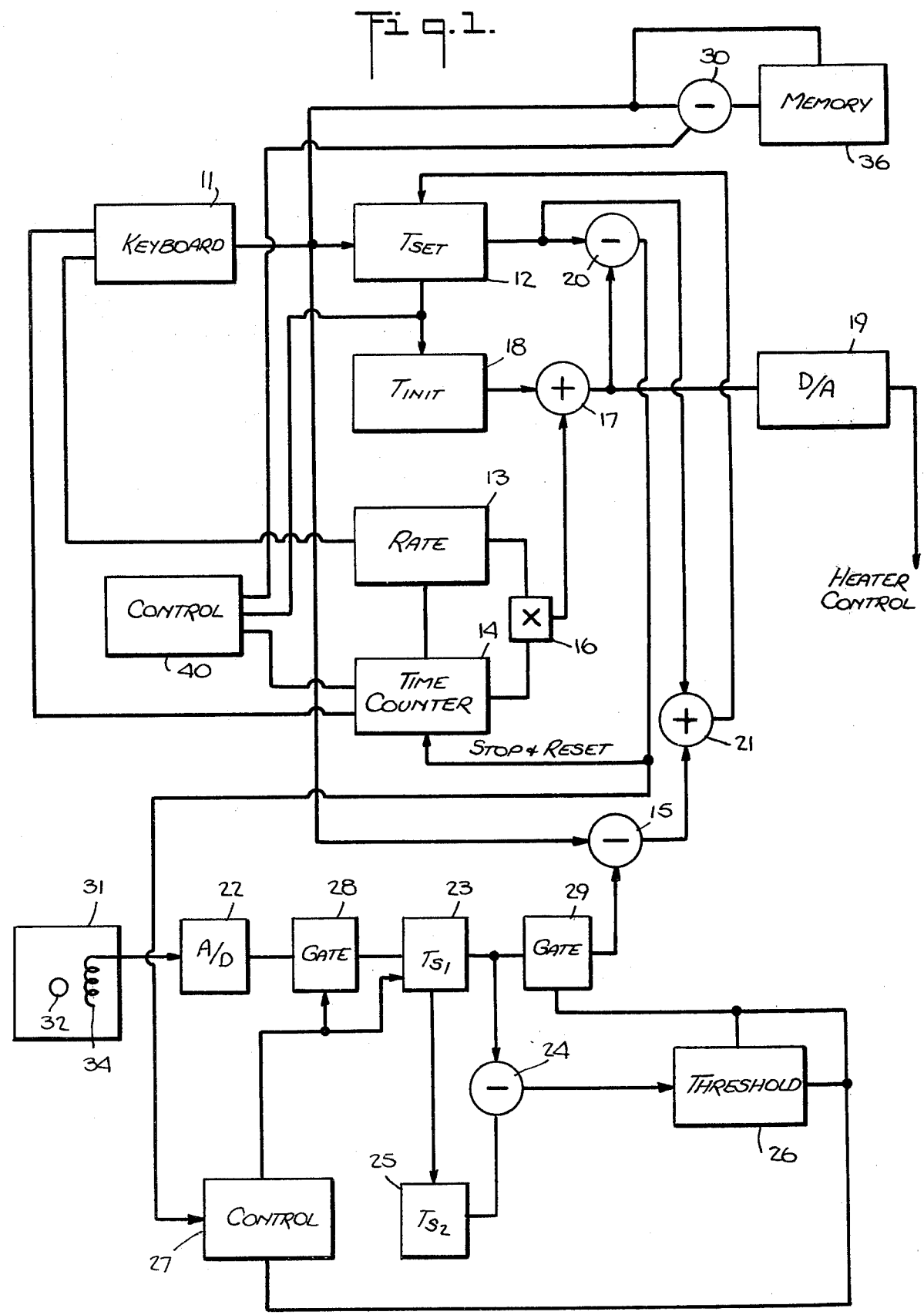
FIG. 1 is a block diagram of the automatic calibration system of the present invention.

Referring to FIG. 1, there is shown the automatic temperature calibrator used in the present invention. A keyboard 11 has output terminals coupled to the T set register 12, a rate register 13 and an elapsed time counter 14. The keyboard input terminal to T set register 12 is also connected to subtractor 15.

The output terminals of rate register 13 and elapsed time counter 14 are connected to a multiplier 16 whose output terminal serves as one input to algebraic adder 17.

A T init register 18 which contain the last temperature to which the system was set prior to the current scan provides a second input to algebraic adder 17. The output terminal of adder 17 is connected to a digital to analog converter 19. As will be described more fully below, the output of adder 17 provides in digital form a continuous output representative of the oven set temperature which is converted into analog form by the digital to analog converter 19 for use in changing oven temperature in accordance therewith.

In addition, the output terminal of adder 17 is connected to subtractor 20 which has a second input terminal from T set register 12.

The output terminal of T set register 12 is connected to adder 21 whose output terminal is connected to T set register 12.

An analog to digital converter 22 continuously receives the temperature of the sample 32 disposed within an oven 31. A thermocouple 34 disposed near the sample 32 may, for example, be used to sense and convert the temperature of the sample 32 to an analog voltage. The analog voltage representative of actual sample temperature is converted to digital form by means of the analog to digital converter 22.

The analog to digital converter 22 has an output terminal connected to a gate 28 whose output terminal is connected to Ts1 register 23. The Ts1 register 23 is connected to subtractor 24 and also to Ts2 register 25. The output terminal of Ts1 register 23 is connected to subtractor 15 via a gate 29. The output terminal of substractor 24 is connected to a threshold circuit 26. The threshold circuit 26 determines when the output of subtractor 24 is zero within predetermined limits i.e. when the registered temperatures in registers 23 and 25 are equal within a predetermined limit. The threshold circuit provides an output pulse to control 27 when this condition of equality is met.

The control 27 has an output terminal connected to gate 28 and Ts1 register 23.

The control 27 includes a clock pulse source to provide a recurring pulse which periodically opens gate 28 to permit a current sample temperature to be registered in the Ts1 register 23. Simultaneously, the pulse is applied to Ts1 register to cause the temperature recorded in Ts1 register 23 to be transferred to the Ts2 register. During the interval between pulses, a comparison of the two temperatures in registers 23 and 25 is made in comparator or subtractor 24. This process of periodically placing the current sample temperature in register 23, transferring the contents of register 23 into register 25 is continued until the two temperatures are equal within predetermined limits. When the two temperatures in registers 23 and 25 are equal, the sample temperature has reached a state of equilibrium and the clock pulse source in control 27 is disabled by the pulse from the threshold circuit 26. The pulse from the threshold circuit is also used to open gate 29 to provide the stabilized temperature as an input to subtractor 15.

In operation, an operator uses the keyboard 11 to select a T set temperature which, for example, may be T MIN. The rate i.e. degrees per unit time is also selected. The rate determines the rate of temperature increase or decrease of the oven. When the operator pushes a calibrate button (not shown) the time counter 14 is started. The elapsed time and rate are continuously multiplied in multiplier 16 and added to the temperature stored in register 18 which is the initial or starting temperature of the oven. The output of adder 17 is applied to subtractor or comparator 20. When the two inputs to subtractor 20 are equal, the time counter is stopped by a pulse from the subtractor 20. This pulse also is applied to control 27 to initiate the clock pulse source therein which had previously been disabled by the pulse from threshold circuit 26 indicative of sample temperature stability.

The cycle of opening and closing gate 29, adding the difference between sample and originally selected temperature to the previous Tset temperature, and programming to the new Tset temperature continues until the output from the digital to analog converter 19 changes oven temperature sufficiently so that sample temperature equals the originally selected temperature. At this point the output of subtractor 15 equals zero.

A control 40 is utilized to gate subtractor 30 only when the difference of the inputs to subtractor 30 is zero thereby assuring that the difference stored in memory 36 is stabilized.

Additionally control 40 is used to control transfer of the contents of register 12 to register 18 and restart counter 14 at the appropriate time i.e. when each new comparison at subtractor 15 is not zero.

After equilibrium is reached, actual sample temperature from gate 29 is compared in subtractor 15 with the keyed in temperature. If there is a difference, it is added to the temperature in register 22 in adder 21 and inserted in register 12. The original temperature registered in register 12 is simultaneously transferred to register 18 and is the new initial temperature of the program.

The sample temperature which has changed as a result of oven temperature responding to the output of digital to analog converter 19 is compared as previously described. At stability, as determined by threshold circuit 26, gate 29 is opened and sample temperature and originally entered temperature are compared and the difference is added to the temperature in register 12. The process is repeated until the originally entered temperature equals sample temperature.

When the temperature originally entered i.e. T MIN equals the sample temperature, the output from subtractor 15 is zero and the output from adder 17 equals the temperature registered in register 12. Digital to analog converter 19 then has an output representative of what the oven temperature should be for sample temperature to be equal to the T MIN temperature. At this point, the system is calibrated at the point T MIN.

The difference between the original keyed in T MIN and the final stabilized output from adder 17 is $\Delta$ T MIN. This difference is taken by subtractor 30 and put in computer memory 36 for reasons to be discussed hereinafter. The original T MIN is also stored in the computer memory. The process must be repeated for T MID and T MAX.

As aforesaid, the system is calibrated at three points in the temperature range. Thus, three temperatures, a minimum temperature, a maximum temperature and a midpoint temperature which is one half the difference between the minimum temperature, are chosen. For convenience, these three temperatures are hereinafter referred to as T MIN, T MAX and T MID, respectively.

The system is calibrated at each point automatically by keying in T MIN and initiating the calibration routine. When the cycle is complete, the actual sample temperature will always be equal to T MIN when T MIN is the selected temperature. The system is calibrated for T MAX in a similar fashion and when the routine is complete, actual sample temperature will always be equal to T MAX when T MAX is selected. This system is calibrated to T MID i.e. T MAX−T MIN divided by two in a like manner and, thereafter, actual sample temperature will equal T MID when T MID is the selected temperature.

While calibration at the three points is adequate for most purposes, it should be noted that the system may be calibrated at more than three points since accuracy increases as calibration points are added.

Figure 2:
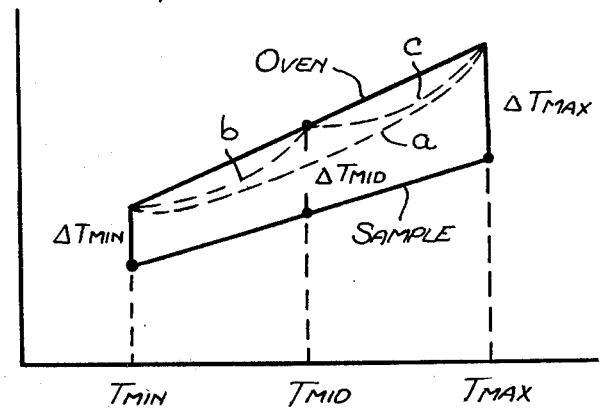
FIG. 2 is a graphical representation of the relationship of certain parameters of the present invention.

FIG. 2 illustrates the relationship between sample and oven temperatures. It can be seen that for the sample to be at T MIN the oven has to be at T MIN+$\Delta$T MIN. Likewise $\Delta$ T MID and $\Delta$ T MAX have to be added to T MID and T MAX to maintain the sample at T MID and T MAX, respectively.

As aforesaid, at the calibration points T MIN, T MID and T MAX, the sample is made to agree exactly with the selected calibration points. However, when a temperature between T MIN and T MID or between T MID and T MAX is selected, the system interpolates by adding a correction factor to the called for oven temperature for each sample temperature selected.

Use of three calibration points and, therefore, two correction factors makes the system more accurate than if two calibration points were used inasmuch as oven temperature deviation from selected sample temperature may not necessarily be linear. This may be readily seen in FIG. 2 where the non-linearity is shown by a dotted line a between T MIN and T MAX if there were no T MID calibration. Dotted lines b and c represent the effect of the same non-linearity when there is a T MID calibration point and actual sample temperature is forced to agree with selected sample temperature at three points instead of two.

The temperature to which the oven has to be corrected is given by $$T\text{ oven} = T + \Delta Tj + \Delta j(T - tj)$$

where
T = uncorrected program temperature and when T is less than T MID $$Tj = T \text{ MIN}$$

$$\Delta j = (\Delta T \text{ MID} - \Delta T \text{ MIN})/(T \text{ MID} - T \text{ MIN})$$

and when T is greater than T MID $$Tj = T \text{ MID}$$

$$\Delta j = (\Delta T \text{ MAX} - \Delta T \text{ MID})/(T \text{ MAX} - T \text{ MID})$$

As may be seen the Δ j terms provide the correction factor to the oven temperature between T MIN and T MID and between T MID and T MAX.

After calibration is complete, the correction factor is used to calculate the necessary oven temperature for any sample temperature at a single point or as the selected temperature is changing. The present invention automatically corrects for differences between actual and required oven temperatures by automatically calculating the required oven temperature for any selected sample temperature. Thus, for any selected sample temperature microprocessor circuit 35 of FIG. 3 in conjunction with memory 36 provides an output in digital form representative of the required oven temperature which is converted to analog form in digital to analog converter 19 which is used in the closed loop system of FIG. 3 to correct oven temperature.

Figure 3:
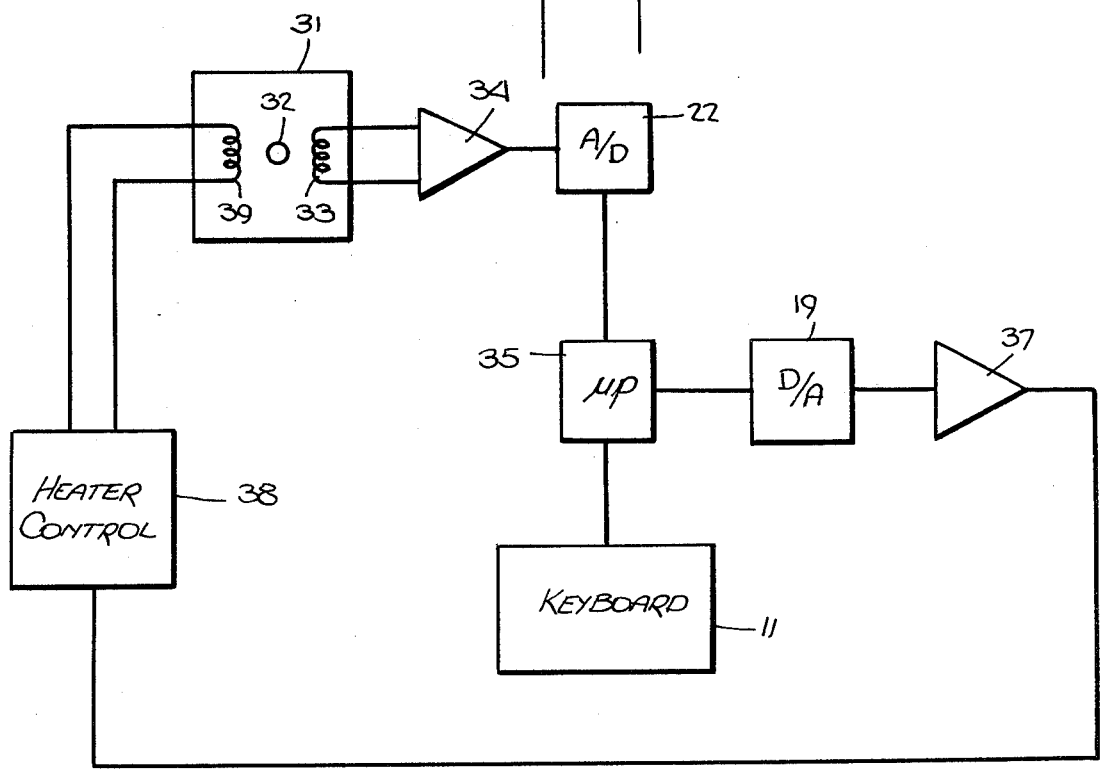
FIG. 3 is a block diagram of the control loop incorporating the present invention.

FIG. 3 illustrates an oven 31 containing a test sample 32 mounted within the oven in any convenient manner. A thermocouple 33 is disposed in close proximity to test sample 32 and provides a volage representative of test sample temperature. This voltage is connected to microprocessor or computer 35 via amplifier 34 and the analog to digital converter 22. The keyboard 11 is connected to microprocessor 35 whose output is connected to a heater control 38 via the digital to analog 19 and amplifier 37.

The oven 31 has disposed therein a combination heating and temperature sensing element 39 which is connected to heater control unit 38.

The output of amplifier 37 is proportional to what the oven temperature must be to maintain sample temperature at any selected value. The element 39 has a temperature sensing portion which senses the temperature of the oven 31 and provides a voltage proportional thereto to the heater control 38. The difference between the demand temperature voltage from amplifier 37 and element 39 is a precise indication of the change that is required. Since this change in temperature may be to lower as well as to raise the temperature of the oven 31, the voltage difference may be used to regulate the duty cycle of the voltage to the heater portion of element 39 until the two voltages are equal. Other well known ways may be used to change oven temperature by use of the voltage difference.

The microprocessor 35 houses the automatic calibration system of FIG. 1 as well as the memory 36. It also houses any standard type of processor unit which in conjunction with memory 36 inserts the correction factor into called for oven temperature.

Thus, once calibration is complete and the T MIN, T MID, T MAX, T MIN, T MID and T MAX are stored in memory 36, the microprocessor 35 continuously solves the above equation to add or subtract the correction factor onto the selected temperature. The correction factor utilized is a function of T e.g. whether it's between T MIN and T MID or T MID and T MAX. The correction factor is added to the called for temperature even as the called for temperature is changing, e.g. ramping up to a selected temperature from a lower or higher initial temperature and follows the slope of oven temperature shown in FIG. 2.

The above described invention should not be construed as limiting the present invention in any way other than as limited by the Claims which follow.

What is claimed is:

1. A thermal analysis system for heating or cooling a test sample to one or more temperatures within a predetermined temperature scale, comprising in combination:
   an oven,
   a sample disposed in said oven,
   first means providing a signal proportional to the temperature of said sample,
   second means providing a signal proportional to the temperature of the oven including heater means for raising the temperature of the oven,
   computer means disposed between said first and second means for correcting automatically for discrepancies between oven temperatures and desired sample temperatures.

2. A thermal analysis system according to claim 1 wherein said computer means comprises,
   calibration means for calibrating the system to at least three selected sample temperatures for causing actual sample temperatures to agree with any one of the three selected temperatures called for by the system.

3. A thermal analysis system according to claim 2 wherein said computer means further comprises,
   correction means for providing a correction to the system for the continuum of temperatures between the calibration points.

4. A thermal analysis system according to claim 3 wherein said calibration means comprises,
   first subtractor means
   first circuit means connected to said first means providing a digital output representative of sample temperature as one input to said first subtractor means,
   input means connected to said first subtractor means for providing a selected sample temperature as a second input to said first subtractor means whereby said first subtractor means determines the difference between actual sample temperature and said selected sample temperature.

5. A thermal analysis system according to claim 4 wherein said calibration means further includes
   second circuit means connected to said first subtractor means responsible to a difference between selected and actual sample temperature for changing oven temperature until said difference is zero.

6. A thermal analysis system according to claim 5 wherein said second circuit means further includes,
   first register means connected to said input means for storing the selected sample temperature,
   first adder means connected to first register means and said first subtractor means having an output terminal connected to said first register means and said first subtractor means having an output terminal connected to said first register means whereby said first register means is updated by each new sum in said first adder means.

7. A thermal analysis system according to claim 6 wherein said second circuit means further includes,
second register means normally storing the initial temperature of the system and connected to said first register means to receive the contents of said first register means when said first register means is updated.

8. A thermal analysis system according to claim 7 wherein said second circuit means further includes,
second adder means connected to said second register means,
selector means connected to said second adder means for selecting a new system temperature,
means connecting said adder means to said heater means whereby the oven temperature is changed from asid initial temperature to said new system temperature.

9. A thermal analysis system according to claim 8 wherein said computer means further comprises
memory means connected to said input means,
third subtractor means connected to said memory means,
said third subtractor means having inputs from said input means and said second adder means for storing each selected temperature and the difference between a selected temperature and the temperature on the output of said second adder means.

10. A thermal analysis system according to claim 9 wherein said selector means comprises,
a rate register,
a time counter connected to said second sbutractor means,
multiplier means connected to said rate register and time counter for multiplying the output therefrom and to said second adder means,
said time counter being stopped when the inputs to said second subtractor means are equal.

11. A thermal analysis system according to claim 10 further including
first control means connected to said time counter and said first subtractor for restarting said time counter when the inputs to said first subtractor are unequal.

12. A thermal analysis system according to claim 11 further including,
second control connected to said first subtractor means for gating said third subtractor means when said first subtractor means has a zero output,
said second control means responsive to a non-zero output from said first subtractor to restart said time counter, 13. A thermal analysis system according to claim 12 wherein
said system is calibrated at a first selected temperature T MIN at the low end of the temperature scale, at a second selected temperature T MAX at the high end of the temperature scale and at a third selected temperature T MIN which is one half the difference between T MAX and T MIN, and
said computer means calculates the correction according to the formula when the called for temperature is less than T MID, $$T \text{ oven} = T + \Delta T \text{MIN} + \left[ \frac{\Delta T \text{MID} - \Delta T \text{MIN}}{T \text{MID} - T \text{MIN}} \right] \times (T - T \text{MIN})$$

and when the called for temperature is greater than T MID $$T \text{ oven} = T + \Delta T \text{MID} + \left[ \frac{\Delta T \text{MAX} - \Delta T \text{MID}}{T \text{MID} - T \text{MIN}} \right] \times (T - T \text{MID})$$

where
T oven = required oven temperature
T = uncorrected temperature
$\Delta$ T MIN, $\Delta$ T MID, $\Delta$ T MAX = difference between selected sample temperature and actual oven temperature to maintain sample at the selected temperature T MIN, T MID and T MAX, respectively.

14. A system for use in a thermal analysis system for testing a sample through a continuum of temperatures,
first means forcing the sample temperature to agree precisely with called for temperatures at a plurality of calibration points,
second means connected to said first means for providing a correction to the system to cause the sample temperature to approximate the called for temperatures in the continuum of temperatures between calibration points.

15. A system according to claim 14 wherein said second means comprises microprocessor means,
memory means included in said microprocessor means for storing each of said calibration point temperature and the difference between each calibration point temperature and the temperature required to force the sample temperature to agree with the selected calibration point temperature.

* * * * *

UNITED STATES PATENT AND TRADEMARK OFFICE
CERTIFICATE OF CORRECTION

PATENT NO. : 4,246,641

DATED : January 20, 1981

INVENTOR(S) : Simon Babil et al.

It is certified that error appears in the above-identified patent and that said Letters Patent are hereby corrected as shown below:

Column 6, line 2, change "T MIN, T MID and T MAX ARE" to --are--.

Column 6, line 45, change "means" to --means,--.

Column 6, line 57, change "includes" to --includes,--.

Column 7, line 21, change "asid" to --said--.

Column 7, line 37, change "sbutractor" to --subtractor--.

Column 7, line 45, change "including" to --including,--.

Column 3, line 59, change "22" to -- 12 --.

Column 5, line 39, change "volage" to -- voltage --.

Column 6, line 66, change "to first" to -- to said first --.

Column 8, line 3, change "counter," to -- counter. --.

Signed and Sealed this

Twenth-eighth Day of September 1982

[SEAL]

Attest:

GERALD J. MOSSINGHOFF

Attesting Officer    Commissioner of Patents and Trademarks